US009805245B2

(12) United States Patent
Shimahara

(10) Patent No.: US 9,805,245 B2
(45) Date of Patent: Oct. 31, 2017

(54) IMAGE RESOLUTION RECOGNITION DEVICE, METHOD FOR RECOGNIZING IMAGE RESOLUTION AND IMAGE RESOLUTION RECOGNITION PROGRAM

(71) Applicant: NEC Corporation, Tokyo (JP)

(72) Inventor: Tatsuya Shimahara, Tokyo (JP)

(73) Assignee: NEC Corporation, Tokyo (JP)

(*) Notice: Subject to any disclaimer, the term of this patent is extended or adjusted under 35 U.S.C. 154(b) by 280 days.

(21) Appl. No.: 14/763,133

(22) PCT Filed: Oct. 31, 2013

(86) PCT No.: PCT/JP2013/079620
§ 371 (c)(1),
(2) Date: Jul. 23, 2015

(87) PCT Pub. No.: WO2014/119071
PCT Pub. Date: Aug. 7, 2014

(65) Prior Publication Data
US 2015/0379326 A1 Dec. 31, 2015

(30) Foreign Application Priority Data
Jan. 31, 2013 (JP) ................................. 2013-017010

(51) Int. Cl.
G06K 9/00 (2006.01)
A61B 5/1172 (2016.01)

(52) U.S. Cl.
CPC ........ *G06K 9/00067* (2013.01); *A61B 5/1172* (2013.01); *G06K 9/0002* (2013.01); *G06K 9/0008* (2013.01); *G06K 9/00087* (2013.01)

(58) Field of Classification Search
CPC ........... G06K 9/00067; G06K 9/00087; G06K 9/0002; G06K 9/0008; A61B 5/1172
See application file for complete search history.

(56) References Cited

U.S. PATENT DOCUMENTS 6,320,641 B1* 11/2001 Bauer ............... G01N 21/8806
348/E5.029

FOREIGN PATENT DOCUMENTS

JP 2004-237087 A 8/2004
JP 2004-280360 A 10/2004
(Continued)

OTHER PUBLICATIONS

International Search Report (ISR) (PCT Form PCT/ISA/210), in PCT/JP2013/079620, dated Dec. 10, 2013.
English Translation of PCT/ISA/237.

*Primary Examiner* — Chan Park
*Assistant Examiner* — Elisa Rice
(74) *Attorney, Agent, or Firm* — McGinn IP Law Group, PLLC

(57) ABSTRACT

To accurately show the size of a standard resolution on an image of a fingerprint. A device comprises: a starting point setting unit (12) which, according to a starting point specification instruction that is input on a scale included in a fingerprint image, sets a starting point on a pilot wire that is specified first by the starting point specification instruction out of pilot wires of divisions on the scale; a passage point setting unit (13) which, every time an input line that is drawn along the scale from the starting point passes a pilot wire, sets a passage point on the passed pilot wire; an inter-division distance calculation unit (14) which calculates an inter-division distance on the image using the position of the starting point and the position of the passage point; a standard resolution calculation unit (15) which calculates the size of a standard resolution that corresponds to the image using the inter-division distance and a unit length which is the length of one division in the scale; and a frame display unit (16) which displays a frame on the image so as to match the size in the standard resolution.

17 Claims, 5 Drawing Sheets

(56) References Cited

FOREIGN PATENT DOCUMENTS

| JP | 2007-207256 A | 8/2007 |
|---|---|---|
| WO | WO 2012/063708 A1 | 5/2012 |

* cited by examiner

IMAGE RESOLUTION RECOGNITION DEVICE, METHOD FOR RECOGNIZING IMAGE RESOLUTION AND IMAGE RESOLUTION RECOGNITION PROGRAM

TECHNICAL FIELD

The present invention relates to an image resolution recognition device, a method for recognizing image resolution, and an image resolution recognition program.

BACKGROUND ART

Fingerprints are utilized as important evidentiary materials when criminals are specified in criminal investigations because fingerprints have characteristics of varying from person to person and remaining unchanged even after the elapse of a long period of time. In criminal investigations, criminals are specified by taking a photograph of a remaining fingerprint collected at a crime scene with a camera, incorporating the image of the remaining fingerprint into a fingerprint collation system, and detecting a fingerprint corresponding to the remaining fingerprint. Images registered with the fingerprint collation system are registered in dispersed states with respect to image quality and resolution because different people take photographs using different cameras. PTL1 below discloses a technique that improves collation accuracy of remaining fingerprint images in poor quality.

CITATION LIST

Patent Literature

PTL1: International Publication No. WO 2012/063708

SUMMARY OF INVENTION

Technical Problem

When fingerprints are collated, it is necessary to collate the fingerprints at a unified standard size, in collation technologies including the collation technology described in PTL1 above. Therefore, when fingerprint collation is performed using an image of a remaining fingerprint photographed with a camera, a fingerprint part of the size of standard resolution for the fingerprint collation is cut out from the photographed image to perform the collation. Incidentally, information on resolution does not stay on a photographed image, and therefore, a scale that functions as a standard in specifying the resolution is photographed together with the remaining fingerprint when a remaining fingerprint is photographed at a crime scene. Among images that photographed remaining fingerprints, however, there exist images in which the scale is not photographed well enough; such images are likely to cause an error in the size of the standard resolution to be cut out, and become a factor to lower collation accuracy of fingerprints.

The present invention is made to solve the above-described problem, and one of its objectives is to provide an image resolution recognition device, a method for recognizing image resolution, and an image resolution recognition program that allow the size of the standard resolution to be accurately represented on a photographed image of a fingerprint.

Solution to Problem

An image resolution recognition device according to an aspect of the present invention includes: a starting point setting unit that sets a starting point on a pilot wire designated first by the starting point specification instruction from among pilot wires to display each division of the scale according to a starting point specification instruction that is input on a scale included in a photographed image of a fingerprint displayed on a display screen; a passing point setting unit that sets a passing point on the passed pilot wire, every time an input line drawn along the scale from the starting point set by the starting point setting unit passes the pilot wire; an inter-division distance calculation unit that calculates inter-division distance on the image using a position of the starting point and positions of the passing points; a standard resolution calculation unit that calculates size of standard resolution corresponding to the image using the inter-division distance calculated by the inter-division distance calculation unit and unit length that is the length of one division of the scale; and a frame display unit that displays a frame on the image in accordance with the size of the standard resolution calculated by the standard resolution calculation unit.

A method for recognizing image resolution according to an aspect of the present invention includes: a starting point setting step that sets a starting point on the pilot wire designated first by the starting point specification instruction from among pilot wires to display each division of the scale according to a starting point specification instruction that is input on a scale included in a photographed image of a fingerprint displayed on a display screen; a passing point setting step that sets a passing point on the passed pilot wire, every time an input line drawn along the scale from the starting point set in the starting point setting step passes the pilot wire; an inter-division distance calculation step that calculates inter-division distance on the image using a position of the starting point and positions of the passing points; a standard resolution calculation step that calculates size of standard resolution corresponding to the image using the inter-division distance calculated in the inter-division distance calculation step and unit length that is the length of one division of the scale; and a frame display step that displays a frame on the image in accordance with the size of the standard resolution calculated in the standard resolution calculation step.

An image resolution recognition program according to an aspect of the present invention causes a computer to execute: a starting point setting step that sets a starting point on the pilot wire designated first by the starting point specification instruction from among pilot wires to display each division of the scale according to a starting point specification instruction that is input on a scale included in a photographed image of a fingerprint displayed on a display screen; a passing point setting step that sets a passing point on the passed pilot wire, every time an input line drawn along the scale from the starting point set in the starting point setting step passes a pilot wire; an inter-division distance calculation step that calculates inter-division distance on the image using a position of the starting point and positions of the passing points; a standard resolution calculation step that calculates size of standard resolution corresponding to the image using the inter-division distance calculated in the inter-division distance calculation step and unit length that is the length of one division of the scale; and a frame display step that displays a frame on the image in accordance with the size of the standard resolution calculated in the standard resolution calculation step.

Advantageous Effects of Invention

According to the present invention, the size of standard resolution can be accurately represented on a photographed image of a fingerprint.

DESCRIPTION OF EMBODIMENTS

Preferred exemplary embodiments of an image resolution recognition device, a method for recognizing image resolution, and an image resolution recognition program according to the present invention will be illustrated below referring to the attached drawings.

Figure 1:
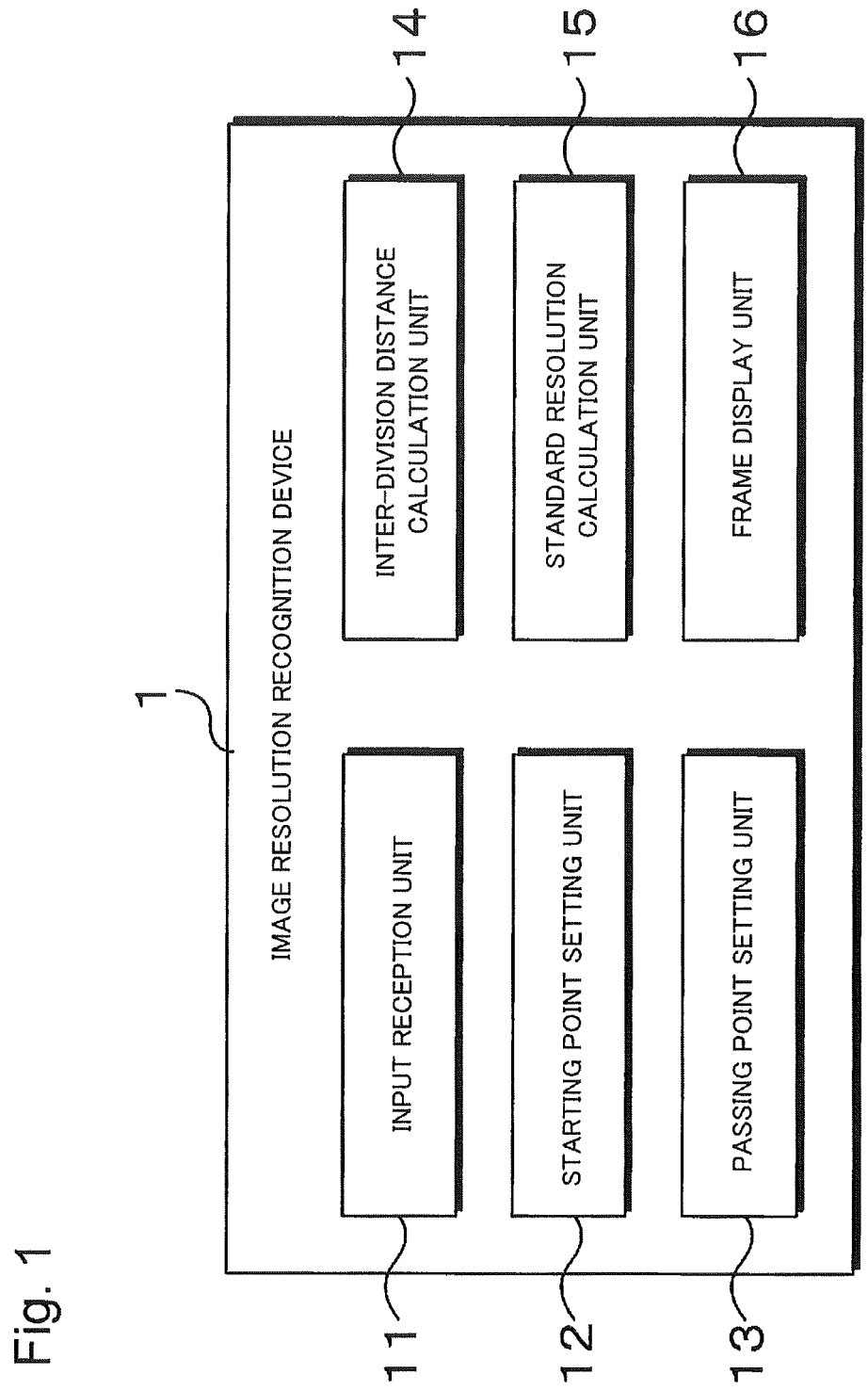
FIG. 1 is a diagram depicting a configuration of an image resolution recognition device in an exemplary embodiment.

First, a configuration of the image resolution recognition device in an exemplary embodiment will be illustrated referring to FIG. 1. An image resolution recognition device 1 has a function to cut out, before registering a fingerprint image photographed with a camera with the fingerprint collation system, a fingerprint part from the fingerprint image at resolution adopted by a fingerprint collation system (hereinafter also called "standard resolution"). In the exemplary embodiment, a case in which the size of the standard resolution adopted by the fingerprint collation system is exemplarily 500 ppi (512 pixels by 512 pixels) is described.

The image resolution recognition device 1 includes, for example, an input reception unit 11, a starting point setting unit 12, a passing point setting unit 13, an inter-division distance calculation unit 14, a standard resolution calculation unit 15, and a frame display unit 16 from the viewpoint of functions.

The image resolution recognition device 1 physically includes, for example, a CPU (Central Processing Unit), a storage unit, an input device, and a display device. The storage unit includes, for example, a ROM (Read Only Memory) and an HDD (Hard Disk Drive) for storing programs and data processed by the CPU, and a RAM (Random Access Memory) used as various types of working areas mainly for control processing. The input device includes, for example, a mouse, a keyboard, and a tablet. These components are connected with each other via a bus. The CPU executes a program stored in the ROM, processes an instruction command input from the input device and data and the like loaded in the RAM, and thereby realizes a function of each unit in the image resolution recognition device 1.

The input reception unit 11 depicted in FIG. 1 receives input of the length of one division (hereinafter also called "unit length") of a scale included in the fingerprint image displayed on the display screen. As the unit length, for example, 1 mm or 5 mm can be used. Input of the unit length may be performed by presenting a preset plurality of lengths on the display screen and letting a user select any one of the presented lengths, or by letting the user directly input the unit length.

Figure 2:
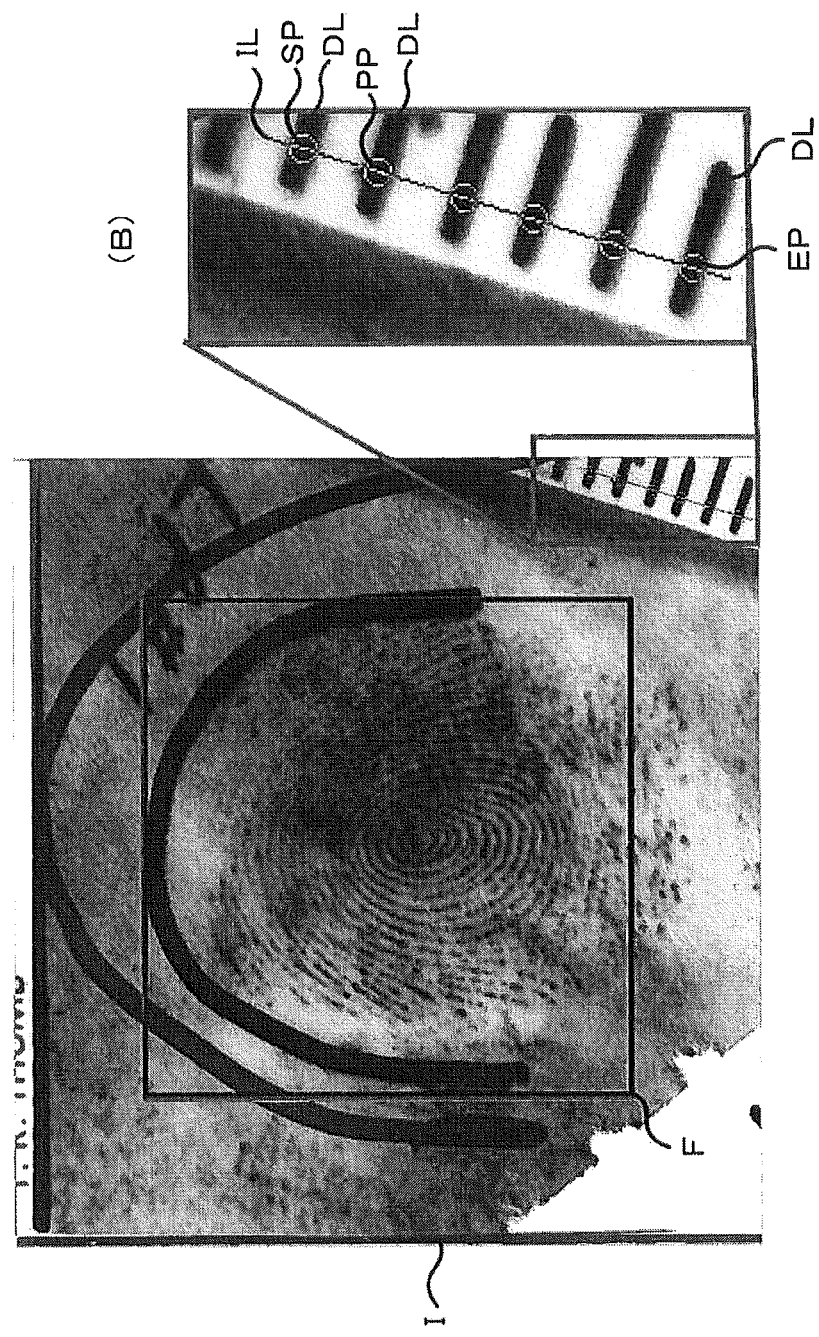
FIG. 2 is a diagram depicting a fingerprint image. (A) is a diagram depicting a fingerprint image in which a fingerprint and a scale are photographed together, and (B) is a diagram depicting the fingerprint image of (A) of which scale part is enlarged to be displayed.

The starting point setting unit 12 sets a starting point on a pilot wire indicating a division of the scale included in the fingerprint image. Specific illustration will be given referring to FIG. 2. FIG. 2(A) is a diagram depicting a fingerprint image in which a fingerprint and a scale are photographed together, and FIG. 2(B) is a diagram depicting the fingerprint image of (A) of which scale part is enlarged to be displayed.

As depicted in FIG. 2(B), a starting point SP is set on a pilot wire DL that an input line IL drawn by an input instruction (starting point specification instruction) given on the scale, for example, with a mouse pointer first passes. The center of the starting point SP is situated at the center of a width direction of the pilot wire DL.

Every time the input line drawn along a longitudinal direction of the scale from the starting point set by the starting point setting unit 12 passes a pilot wire, the passing point setting unit 13 depicted in FIG. 1 sets a passing point on the passed pilot wire. When the passing point setting unit 13 detects that the input of the input line is finished, a passing point on the pilot wire that passes last is made to be an end point. The setting of a passing point will be specifically depicting referring to FIG. 2.

As depicted in FIG. 2(B), a passing point PP is set respectively on each pilot wire DL that the input line IL drawn along the longitudinal direction of the scale with the mouse pointer has passed. The center of the passing point PP is situated at the center of the width direction of the pilot wire DL. When the input instruction on the input line IL is finished, a passing point set on the pilot wire DL that passes last is made to be an end point EP.

Figure 3:
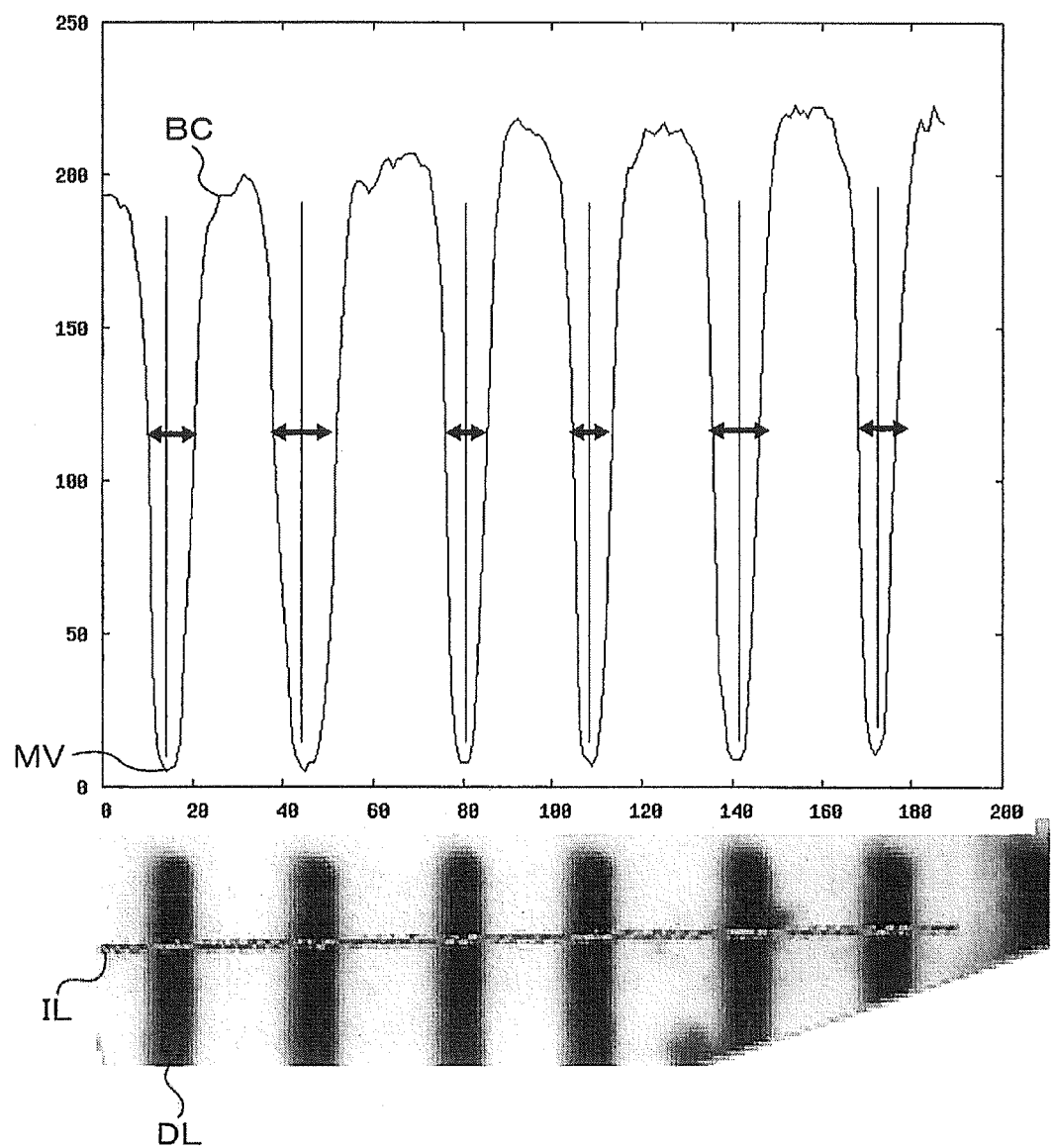
FIG. 3 is a diagram depicting a luminance value curve on an image on which an input line is drawn.

It is possible to determine whether the input line IL has passed a pilot wire DL on the basis of, for example, a luminance value curve on the image on which the input line IL is drawn. Specific illustration will be given referring to FIG. 3. As depicted in FIG. 3, whereas a luminance value is high (in the neighborhood of 200) on the scale other than the pilot wires DL, the luminance value is low (in the neighborhood of 0) on the pilot wires DL. Therefore, it is possible to determine whether the input line IL passed the pilot wires DL by detecting valleys of a luminous value curve BC on the image on which the input line IL is drawn.

In addition, one example of a method for calculating center positions (center of the starting point and the passing points) of the width direction of pilot wires DL will be illustrated referring to FIG. 3. As depicted in FIG. 3, local minimum values MV of the luminance value curve BC are calculated on the basis of the luminance value curve BC on the image on which the input line IL is drawn. Positions on the image corresponding to the calculated respective local minimum values MV are made to be center positions of the width direction of the pilot wires DL.

The inter-division distance calculation unit 14 depicted in FIG. 1 calculates (estimates) inter-division distance on the image using the center position of the starting point set by the starting point setting unit 12 and the center positions of the passing points set by the passing point setting unit 13. When there are a plurality of passing points, an average value of respective distances between the points adjacent to each other among the starting point and the passing points is calculated as the inter-division distance on the image. It is possible to reduce an estimated error of the inter-division distance on the image by increasing passing points, even if there is dispersion in thickness of respective pilot wires by adopting the average value as the inter-division distance.

The inter-division distance calculation unit 14 may calculate the inter-division distance after correcting an inclination of the input line on the basis of an angle of the input line intersecting with a pilot wire. Specifically, the inclination of the input line is corrected so that the angle of the input line intersecting with the pilot wire may be a right angle. Hereby, even in the case that an input line input by the user is drawn such that the input line is not orthogonal to the pilot wire, the inter-division distance can be calculated after correction so that the input line may be orthogonal to the pilot wire that will allow a calculation error to be reduced as much as possible.

The standard resolution calculation unit 15 calculates (estimates) the size of the standard resolution (hereinafter also called "estimated standard resolution") corresponding to the fingerprint image displayed on the display screen using the inter-division distance calculated by the inter-division distance calculation unit 14 and the unit length received by the input reception unit 11

The frame display unit 16 displays a frame on the image according to a display position specification instruction which is input on the display image. The display position specification instruction may be an instruction to designate a range of an outline of the fingerprint, for example. Specifically, when an instruction to designate a range is input by tracing the outline of the fingerprint with the mouse pointer, for example, a frame is set according to the instruction so that a range-designated fingerprint part will be included in the frame. When a frame is set, the center of gravity of a range-designated region may be calculated to set the frame with the center of the gravity in the center.

The frame display unit 16 changes the size of the frame displayed on the fingerprint image in accordance with the size in the estimated standard resolution calculated by the standard resolution calculation unit 15. Specific illustration will be given referring to FIG. 2. As depicted in FIG. 2(A), the size of a frame F displayed on a fingerprint image I is changed so as to be a range indicating the size in the estimated standard resolution calculated by the standard resolution calculation unit 15. In other words, the size of the frame F after change is displayed by the size estimated to correspond to 500 ppi in the fingerprint image I.

Figure 4:
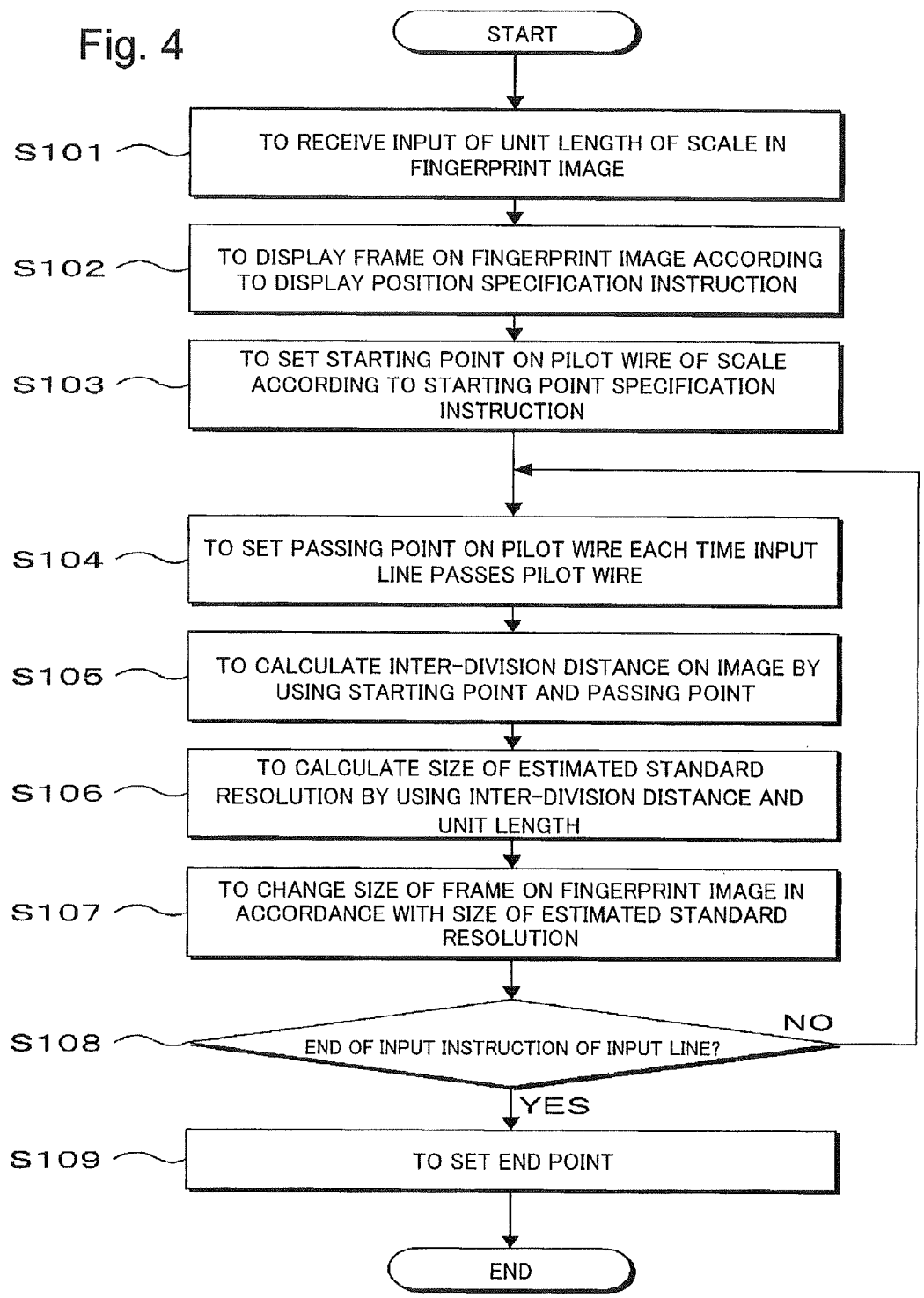
FIG. 4 is a flowchart to illustrate operation when resolution of an image is recognized.

Next, one example of operation at a time of recognizing image resolution will be illustrated referring to FIG. 4.

First, the input reception unit 11 receives an input of unit length of a scale included in a fingerprint image displayed on the display screen (step S101).

Subsequently, the frame display unit 16 displays a frame on the fingerprint image according to a display position specification instruction which is input on the fingerprint image (step S102).

Subsequently, the starting point setting unit 12 sets a starting point on a pilot wire that an input line first passes according to a starting point specification instruction that is input on the scale of the fingerprint image (step S103).

Subsequently, every time the input line drawn along a longitudinal direction of the scale from the starting point set in the step S103 passes a pilot wire, the passing point setting unit 13 sets a passing point on the passed pilot wire (step S104).

Subsequently, the inter-division distance calculation unit 14 calculates inter-division distance on the image by using a center position of the starting point set in the step S103 and center positions of the passing points set in the step S104 (step S105).

Subsequently, the standard resolution calculation unit 15 calculates the size of estimated standard resolution by using the inter-division distance calculated in the step S105 and the unit length received in the step S101 (step S106).

Subsequently, the frame display unit 16 changes the size of the frame displayed on the fingerprint image in accordance with the size in the estimated standard resolution calculated in the step S106 (step S107).

Each processing from the step S104 to the step S107 is repeated while the input instruction of the input line continues (step S108; NO).

On the other hand, when the finish of input instruction of the input line is detected (step S108; YES), the passing point setting unit 13 makes a passing point set on the passed pilot wire last an end point (step S109). Then, the operation is finished.

As described above, according to the image resolution recognition device 1 in the exemplary embodiment, the input reception unit 11 receives the unit length of one division of a scale included in a fingerprint image; the starting point setting unit 12 sets a starting point at a center position of a pilot wire that an input line drawn by an input instruction given on the scale of the fingerprint image first passes; the passing point setting unit 13 sets a passing point at a center position of the pilot wire, every time the input line drawn along the scale from the starting point passes a pilot wire; the inter-division distance calculation unit 14 calculates inter-division distance on the fingerprint image by using the center position of the starting point and the center positions of the passing points; the standard resolution calculation unit 15 calculates the size of standard resolution corresponding to the fingerprint image by using the inter-division distance and the unit length; the frame display unit 16 displays a frame on the fingerprint image in accordance with the size of the standard resolution, and thereby the frame indicating the size of the standard resolution corresponding to the image can be simply and accurately displayed on the fingerprint image.

[Modifications]

The above-described exemplary embodiment is only exemplification, and do not exclude application of various variants or techniques not clearly specified in the exemplary embodiment. In other words, the present invention can be executed in various modified configurations without departing from the scope of the spirit of the present invention.

For example, the above-described exemplary embodiment illustrates the case where the display position specification instruction is an instruction to designate a range of an outline of a fingerprint, but the display position specification instruction is not limited thereto. For example, the display position specification instruction may be an instruction to designate a center position of a frame displayed on the image. In this case, the frame display unit 16 may display a frame of a specific size with the instructed position as a center on the image according to the display position specification instruction. In addition, the display position specification instruction may be made unnecessary. In this case, the frame display unit 16 displays a frame on the image in accordance with the size in the estimated standard resolution initially calculated by the standard resolution calculation unit 15, and then the size of the frame may be changed in accordance with the size of the estimated standard resolution recalculated by the standard resolution calculation unit 15. Further, the display position of the frame displayed on the image may be made arbitrarily movable by, for example, a drag operation.

In the above-described exemplary embodiment, the starting point and the passing points are set at center positions of pilot wires, but positions where the starting point and the passing points are set are not limited thereto. The starting point and the passing points have only to be set on the pilot wires intersecting with an input line. In this case, the inter-division distance calculation unit 14 may calculate inter-division distance by using the position where the starting point is set and the positions where the pilot wires are set.

In the above-described exemplary embodiment, the input of the starting point specification instruction, the input line, the display position specification instruction, and the like is performed by operating the mouse pointer, but a method for input is not limited thereto. For example, when a tablet is provided as an input device, the input of the starting point specification instruction, the input line, the display position specification instruction, and the like may be performed by operating with a finger, a touch pen, or the like on a touch panel.

Figure 5:
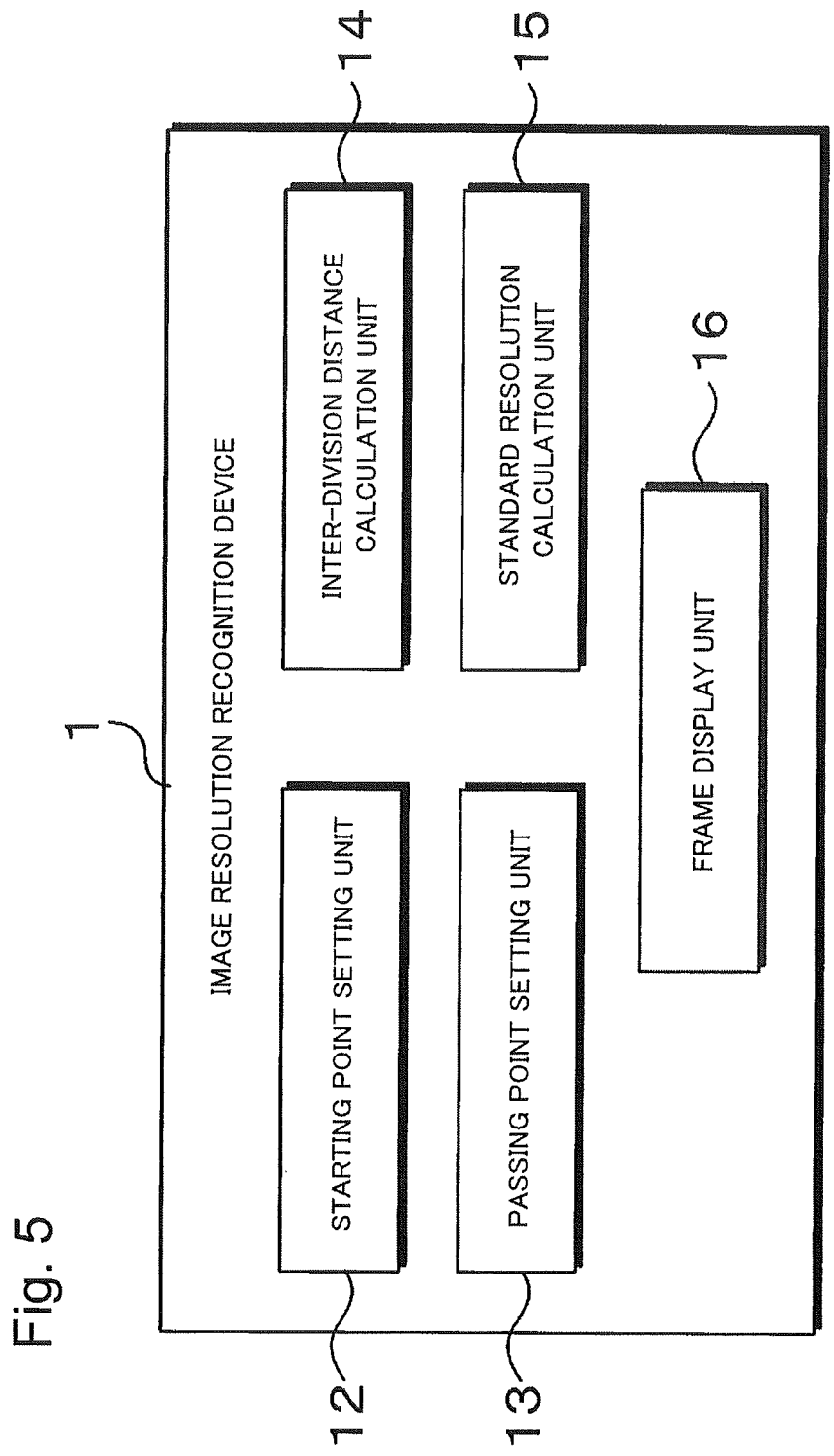
FIG. 5 is a diagram depicting a minimum configuration of an image resolution recognition device according to the present invention.

The image resolution recognition device 1 in the above-described exemplary embodiment has the functions depicted in FIG. 1 as components, but the configuration of the image resolution recognition device 1 according to the present invention is not limited thereto. A minimum configuration of the present invention will be illustrated. FIG. 5 is a diagram depicting the minimum configuration of the image resolution recognition device 1 according to the present invention.

As depicted in FIG. 5, the image resolution recognition device 1 only has to include at least the starting point setting unit 12, the passing point setting unit 13, the inter-division distance calculation unit 14, the standard resolution calculation unit 15, and the frame display unit 16 from the viewpoint of functions.

In this case, unit length is set in advance, and the standard resolution calculation unit 15 may calculate the size in the estimated standard resolution by using the inter-division distance calculated by the inter-division distance calculation unit 14 and the unit length set in advance.

Part or all of the above-described exemplary embodiments can be also described like the following Supplementary Notes, but the present invention is not limited to the following.

(Supplementary Note 1)

An image resolution recognition device including: a starting point setting unit that, according to a starting point specification instruction that is input on a scale included in a photographed image of a fingerprint displayed on a display screen, sets a starting point on a pilot wire designated first by the starting point specification instruction from among the pilot wires to display divisions of the scale; a passing point setting unit that, every time an input line drawn along the scale from the starting point set by the starting point setting unit passes a pilot wire, sets a passing point on the passed pilot wire; an inter-division distance calculation unit that calculates inter-division distance on the image using a position of the starting point and positions of the passing points; a standard resolution calculation unit that calculates size of standard resolution corresponding to the image using the inter-division distance calculated by the inter-division distance calculation unit and unit length that is length of one division of the scale; and a frame display unit that displays a frame on the image in accordance with the size in the standard resolution calculated by the standard resolution calculation unit.

(Supplementary Note 2)

The image resolution recognition device according to Supplementary Note 1, wherein the frame display unit displays a frame on the image according to a display position specification instruction that is input on the image, and changes size of the frame displayed on the image in accordance with the size of the standard resolution calculated by the standard resolution calculation unit.

(Supplementary Note 3)

The image resolution recognition device according to Supplementary Note 2, wherein the display position specification instruction is an instruction to designate a range of an outline of the fingerprint.

(Supplementary Note 4)

The image resolution recognition device according to Supplementary Note 2, wherein the display position specification instruction is an instruction to designate a center position of the frame to be displayed on the image.

(Supplementary Note 5)

The image resolution recognition device according to any of Supplementary Notes 1-4, wherein the inter-division distance calculation unit calculates the inter-division distance after correcting an inclination of the input line on the basis of an angle of the input line intersecting with each of pilot wires at a time of calculating the inter-division distance.

(Supplementary Note 6)

The image resolution recognition device according to any of Supplementary Notes 1-5, further including an input reception unit that receives input of the unit length, wherein the standard resolution calculation unit calculates the size of the standard resolution using the inter-division distance calculated by the inter-division distance calculation unit and the unit length received by the input reception unit.

(Supplementary Note 7)

The image resolution recognition device according to any of Supplementary Notes 1-6, wherein the starting point setting unit sets the starting point at a center position of pilot wire, the passing point setting unit sets the passing points at center positions of the pilot wires, and the inter-division distance calculation unit calculates the inter-division distance using the center position of the starting point and the center positions of the passing points.

(Supplementary Note 8)

A method for recognizing image resolution including: a starting point setting step of, according to a starting point specification instruction that is input on a scale included in a photographed image of a fingerprint displayed on a display screen, setting a starting point on a pilot wire designated first by the starting point specification instruction from among the pilot wires to display divisions of the scale; a passing point setting step of, every time an input line drawn along the scale from the starting point set in the starting point setting step passes a pilot wire, setting a passing point on the passed pilot wire; an inter-division distance calculation step of calculating inter-division distance on the image using a position of the starting point and positions of the passing points; a standard resolution calculation step of calculating size of standard resolution corresponding to the image using the inter-division distance calculated in the inter-division distance calculation step and unit length that is length of one division of the scale; and a frame display step of displaying a frame on the image in accordance with the size of the standard resolution calculated in the standard resolution calculation step.

(Supplementary Note 9)

The method for recognizing image resolution according to Supplementary Note 8, wherein the frame display step includes displaying a frame on the image according to a display position specification instruction that is input on the image, and changing size of the frame displayed on the image in accordance with the size of the standard resolution calculated in the standard resolution calculation step.

(Supplementary Note 10)

The method for recognizing image resolution according to Supplementary Note 9, wherein the display position specification instruction is an instruction to designate a range of an outline of the fingerprint.

(Supplementary Note 11)

The method for recognizing image resolution according to Supplementary Note 9, wherein the display position specification instruction is an instruction to designate a center position of the frame to be displayed on the image.

(Supplementary Note 12)

The method for recognizing image resolution according to any of Supplementary Notes 8-11, wherein the inter-division distance calculation step includes calculating the inter-division distance after correcting an inclination of the input line on the basis of an angle of the input line intersecting with each of pilot wires at a time of calculating the inter-division distance.

(Supplementary Note 13)

The method for recognizing image resolution according to any of Supplementary Notes 8-12, further including an input reception step of receiving input of the unit length, wherein the standard resolution calculation step includes calculating the size of the standard resolution using the inter-division distance calculated in the inter-division distance calculation step and the unit length received in the input reception step.

(Supplementary Note 14)

The method for recognizing image resolution according to any of Supplementary Notes 8-13, wherein the starting point setting step includes setting the starting point at a center position of pilot wire, the passing point setting step includes setting the passing points at center positions of the pilot wires, and the inter-division distance calculation step includes calculating the inter-division distance using the center position of the starting point and the center positions of the passing points.

(Supplementary Note 15)

An image resolution recognition program causing a computer to execute: a starting point setting step of, according to a starting point specification instruction that is input on a scale included in a photographed image of a fingerprint displayed on a display screen, setting a starting point on a pilot wire designated first by the starting point specification instruction from among the pilot wires to display divisions of the scale; a passing point setting step of, every time an input line drawn along the scale from the starting point set in the starting point setting step passes a pilot wire, setting a passing point on the passed pilot wire; an inter-division distance calculation step of calculating inter-division distance on the image using a position of the starting point and positions of the passing points; a standard resolution calculation step of calculating size of standard resolution corresponding to the image using the inter-division distance calculated in the inter-division distance calculation step and unit length that is length of one division of the scale; and a frame display step of displaying a frame on the image in accordance with the size of the standard resolution calculated in the standard resolution calculation step.

(Supplementary Note 16)

The image resolution recognition program according to Supplementary Note 15, wherein the frame display step includes displaying a frame on the image according to a display position specification instruction that is input on the image, and changing size of the frame displayed on the image in accordance with the size of the standard resolution calculated in the standard resolution calculation step.

(Supplementary Note 17)

The image resolution recognition program according to Supplementary Note 16, wherein the display position specification instruction is an instruction to designate a range of an outline of the fingerprint.

(Supplementary Note 18)

The image resolution recognition program according to Supplementary Note 16, wherein the display position specification instruction is an instruction to designate a center position of the frame to be displayed on the image.

(Supplementary Note 19)

The image resolution recognition program according to any of Supplementary Notes 15-18, wherein the inter-division distance calculation step includes calculating the inter-division distance after correcting an inclination of the input line on the basis of an angle of the input line intersecting with each of pilot wires at a time of calculating the inter-division distance.

(Supplementary Note 20)

The image resolution recognition program according to any of Supplementary Notes 15-19, further causing the computer to execute an input reception step of receiving input of the unit length, wherein the standard resolution calculation step includes calculating the size of the standard resolution using the inter-division distance calculated in the inter-division distance calculation step and the unit length received in the input reception step.

(Supplementary Note 21)

The image resolution recognition program according to any of Supplementary Notes 15-20, wherein the starting point setting step includes setting the starting point at a center position of a pilot wire, the passing point setting step includes setting the passing points at center positions of the pilot wires, and the inter-division distance calculation step includes calculating the inter-division distance using the center position of the starting point and the center positions of the passing points.

This application claims the priority based on Japanese Patent Application No. 2013-17010, filed on Jan. 31, 2013, and its disclosure is incorporated herein in its entity.

The present invention is illustrated referring to the exemplary embodiments, but the present invention is not limited to the above-described exemplary embodiments. The configuration and details of the present invention are susceptible to various variants that can be understood by those skilled in the art within the scope of the present invention.

INDUSTRIAL APPLICABILITY

The image resolution recognition device, the method for recognizing image resolution, and the image resolution recognition program according to the present invention are suitable for accurately representing the size of the standard resolution on a photographed image of a fingerprint.

REFERENCE SIGNS LIST

1 Image resolution recognition device
11 Input reception unit
12 Starting point setting unit
13 Passing point setting unit
14 Inter-division distance calculation unit
15 Standard resolution calculation unit
16 Frame display unit

The invention claimed is:

1. An image resolution recognition device comprising:
a starting point setting unit that, according to a starting point specification instruction that is input on a scale included in a photographed image of a fingerprint displayed on a display screen, sets a starting point on a pilot wire designated first by the starting point specification instruction from among the pilot wires to display divisions of the scale;
a passing point setting unit that, every time an input line drawn along the scale from the starting point set by the starting point setting unit passes a pilot wire, sets a passing point on the passed pilot wire;
an inter-division distance calculation unit that calculates inter-division distance on the image using a position of the starting point and positions of the passing points;
a standard resolution calculation unit that calculates size of standard resolution corresponding to the image using the inter-division distance calculated by the inter-division distance calculation unit and unit length that is length of one division of the scale; and
a frame display unit that displays a frame on the image in accordance with the size of the standard resolution calculated by the standard resolution calculation unit.

2. The image resolution recognition device according to claim 1, wherein the frame display unit displays a frame on the image according to a display position specification instruction that is input on the image, and changes size of the frame displayed on the image in accordance with the size of the standard resolution calculated by the standard resolution calculation unit.

3. The image resolution recognition device according to claim 2, wherein the display position specification instruction is an instruction to designate a range of an outline of the fingerprint.

4. The image resolution recognition device according to claim 2,
wherein the display position specification instruction is an instruction to designate a center position of the frame to be displayed on the image.

5. The image resolution recognition device according to claim 1,
wherein the inter-division distance calculation unit calculates the inter-division distance after correcting an inclination of the input line on the basis of an angle of the input line intersecting with each of pilot wires at a time of calculating the inter-division distance.

6. The image resolution recognition device according to claim 1,
further comprising an input reception unit that receives input of the unit length,
wherein the standard resolution calculation unit calculates the size of the standard resolution using the inter-division distance calculated by the inter-division distance calculation unit and the unit length received by the input reception unit.

7. The image resolution recognition device according to claim 1, wherein
the starting point setting unit sets the starting point at a center position of a pilot wire;
the passing point setting unit sets the passing points at center positions of the pilot wires; and
the inter-division distance calculation unit calculates the inter-division distance using the center position of the starting point and the center positions of the passing points.

8. A method for recognizing image resolution comprising:
a starting point setting step of, according to a starting point specification instruction that is input on a scale included in a photographed image of a fingerprint displayed on a display screen, setting a starting point on a pilot wire designated first by the starting point specification instruction from among the pilot wires to display divisions of the scale;
a passing point setting step of, every time an input line drawn along the scale from the starting point set in the starting point setting step passes a pilot wire, setting a passing point on the passed pilot wire;
an inter-division distance calculation step of calculating inter-division distance on the image using a position of the starting point and positions of the passing points;
a standard resolution calculation step of calculating size of standard resolution corresponding to the image using the inter-division distance calculated in the inter-division distance calculation step and unit length that is length of one division of the scale; and
a frame display step of displaying a frame on the image in accordance with the size of the standard resolution calculated in the standard resolution calculation step.

9. The method for recognizing image resolution according to claim 8,
wherein the frame display step includes displaying a frame on the image according to a display position specification instruction that is input on the image, and changing size of the frame displayed on the image in accordance with the size of the standard resolution calculated in the standard resolution calculation step.

10. The method for recognizing image resolution according to claim 8,
wherein the inter-division distance calculation step includes calculating the inter-division distance after correcting an inclination of the input line on the basis of an angle of the input line intersecting with each of pilot wires at a time of calculating the inter-division distance.

11. The method for recognizing image resolution according to claim 8,
further comprising an input reception step of receiving input of the unit length,
wherein the standard resolution calculation step includes calculating the size of the standard resolution using the inter-division distance calculated in the inter-division distance calculation step and the unit length received in the input reception step.

12. The method for recognizing image resolution according to claim 8, wherein
the starting point setting step includes setting the starting point at a center position of a pilot wire;
the passing point setting step includes setting the passing points at center positions of the pilot wires; and
the inter-division distance calculation step includes calculating the inter-division distance using the center position of the starting point and the center positions of the passing points.

13. A non-transitory computer readable medium embodying an image resolution recognition program causing a computer to execute:
a starting point setting step of, according to a starting point specification instruction that is input on a scale included in a photographed image of a fingerprint displayed on a display screen, setting a starting point on a pilot wire designated first by the starting point specification instruction from among the pilot wires to display divisions of the scale;

a passing point setting step of, every time an input line drawn along the scale from the starting point set in the starting point setting step passes a pilot wire, setting a passing point on the passed pilot wire;

an inter-division distance calculation step of calculating inter-division distance on the image using a position of the starting point and positions of the passing points;

a standard resolution calculation step of calculating size of standard resolution corresponding to the image using the inter-division distance calculated in the inter-division distance calculation step and unit length that is length of one division of the scale; and a frame display step of displaying a frame on the image in accordance with the size of the standard resolution calculated in the standard resolution calculation step.

14. The non-transitory computer readable medium according to claim 13, wherein the frame display step includes displaying a frame on the image according to a display position specification instruction that is input on the image, and changing size of the frame displayed on the image in accordance with the size of the standard resolution calculated in the standard resolution calculation step.

15. The non-transitory computer readable medium according to claim 13, wherein the inter-division distance calculation step includes calculating the inter-division distance after correcting an inclination of the input line on the basis of an angle of the input line intersecting with each of pilot wires at a time of calculating the inter-division distance.

16. The non-transitory computer readable medium according to claim 13, embodying the program further causing the computer to execute an input reception step of receiving input of the unit length, wherein the standard resolution calculation step includes calculating the size of the standard resolution using the inter-division distance calculated in the inter-division distance calculation step and the unit length received in the input reception step.

17. The non-transitory computer readable medium according to claim 13, wherein the starting point setting step includes setting the starting point at a center position of a pilot wire;

the passing point setting step includes setting the passing points at center positions of the pilot wires;

and the inter-division distance calculation step includes calculating the inter-division distance using the center position of the starting point and the center positions of the passing points.

* * * * *